United States Patent [19]

Arai et al.

[11] 4,374,764
[45] * Feb. 22, 1983

[54] MACROLIDE ANTIBIOTIC

[75] Inventors: Mamoru Arai; Tatsuo Haneishi; Mutsuo Nakajima, all of Hiromachi, Japan

[73] Assignee: Sankyo Company, Limited, Tokyo, Japan

[*] Notice: The portion of the term of this patent subsequent to Jun. 22, 1999, has been disclaimed.

[21] Appl. No.: 199,238

[22] Filed: Oct. 21, 1980

[30] Foreign Application Priority Data

Nov. 1, 1979 [JP] Japan ................................ 54/141650

[51] Int. Cl.³ ........................................ C07C 103/52
[52] U.S. Cl. ............................................ 260/112.5 R
[58] Field of Search ................................. 260/112.5 R

[56] References Cited

U.S. PATENT DOCUMENTS 3,365,362 1/1968 Mancy et al. ................. 260/112.5 R
3,719,656 3/1973 Jolles ............................ 260/112.5 R
4,108,985 8/1978 Rüegger et al. ............. 260/112.5 R Primary Examiner—Delbert R. Phillips
Attorney, Agent, or Firm—Frishauf, Holtz, Goodman & Woodward

[57] ABSTRACT

Macrolide antibiotics are derivatives of the compound Mycoplanecin and have the formula:

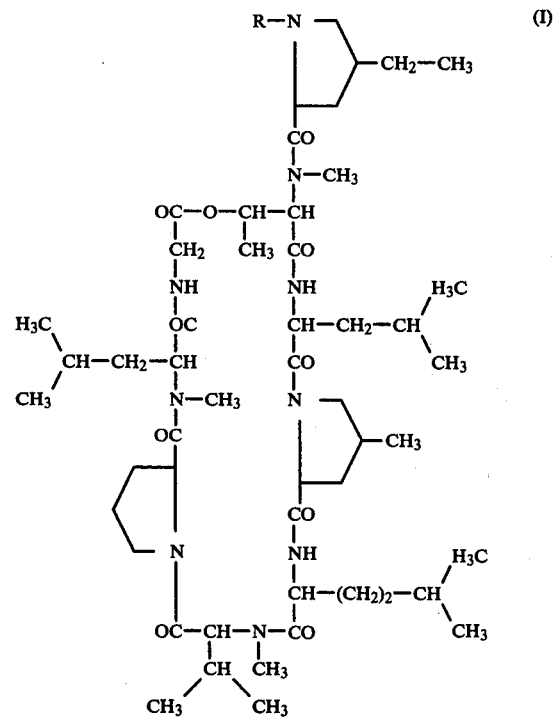

(in which R represents a hydrogen atom or an N-(α-hydroxybutyryl)-N-methylvalyl group). The compound in which R represents an N-(α-hydroxybutyryl)-N-methylvalyl group can be prepared by reducing Mycoplanecin and the compound in which R represents a hydrogen atom can be prepared by the hydrolysis of Mycoplanecin or of the compound of formula (I) in which R represents an N-(α-hydroxybutyryl)-N-methylvalyl group.

3 Claims, No Drawings

MACROLIDE ANTIBIOTIC

BACKGROUND TO THE INVENTION

The present invention relates to certain new macrolide antibiotics which are derivatives of Mycoplanecin.

Mycoplanecin is the subject of co-pending U.S. application Ser. No. 41,501, filed May 22, 1979 issued as U.S. Pat. No. 4,336,249 and has the formula (I) given above except that, in Mycoplanecin, R represents the group:

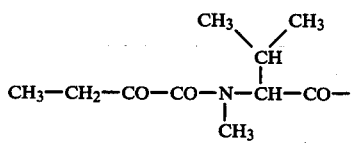

As disclosed in the aforementioned co-pending application, Mycoplanecin has valuable antibiotic properties against a variety of microorganisms, but most especially against microoganisms of the genus Mycobacterium. Mycoplanecin also has a rather low toxicity and, as a result, is expected to be of considerable value in chemotherapy. However, we have now found that the biological availability of Mycoplanecin on administration to animals by the usual routes is rather low and this may restrict, to some extent, the therapeutic value of Mycoplanecin. Accordingly, we considered it desirable to seek derivatives of Mycoplanecin which would retain all, or a substantial proportion, of the Mycoplanecin activity but which have improved absorption on administration to animals.

We have now surprisingly discovered that modification or replacement of the N-(α-ketobutyryl)-N-methylvalyl group of formula:

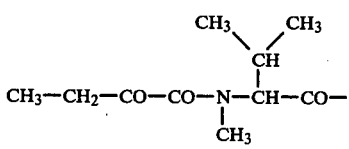

gives compounds having improved biological availability and value as intermediates in the preparation of other Mycoplanecin derivatives.

BRIEF SUMMARY OF INVENTION

In accordance with the present invention, there are provided new compounds of formula (I):

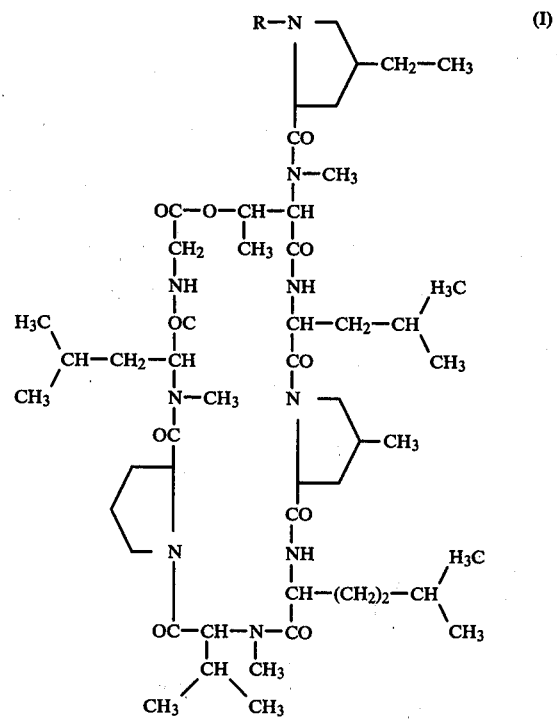

[In which R represents a hydrogen atom or an N-(α-hydroxybutyryl)-N-methylvalyl group]. For convenience, the two compounds represented by formula (I) are hereinafter referred to as compound (II):

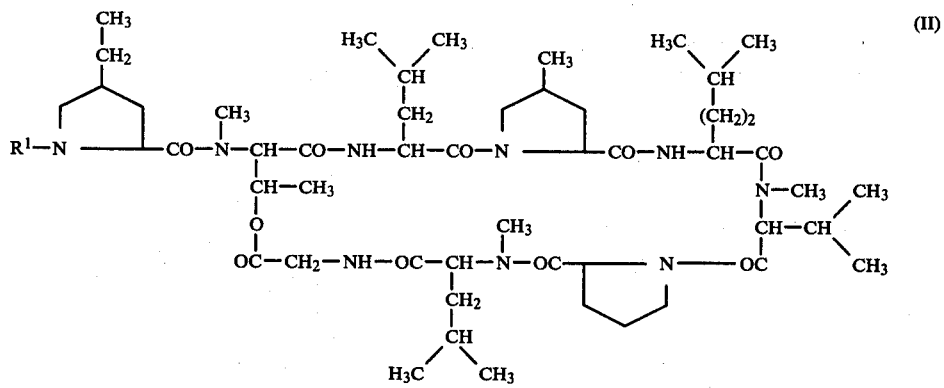

[In which R' represents an N-(α-hydroxybutyryl)-N-methylvalyl group] and compound (III):

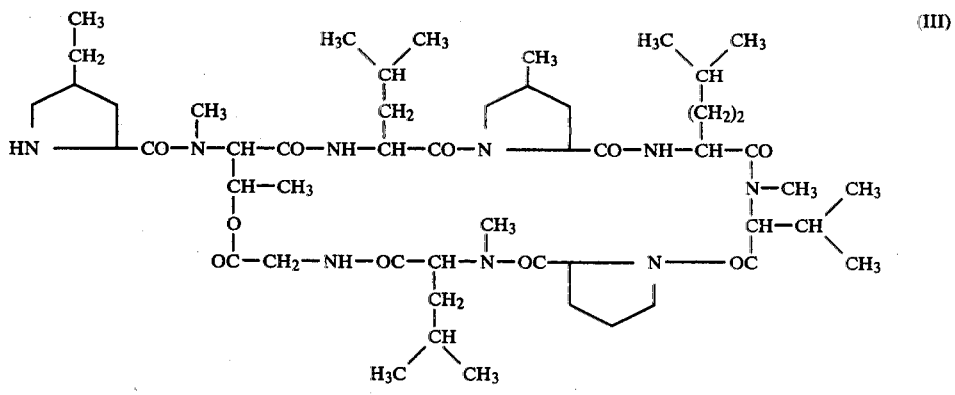

DETAILED DESCRIPTION OF INVENTION

Compound (II) is characterized by the following physical and chemical properties:
1. Colour and state
Colourless needles.
2. Melting point
175°–182° C.
3. Specific rotation
$[\alpha]_D^{25} -69.1°$ (c=1.02, chloroform).
4. Elemental analysis
C, 60.74%; H, 8.84%; N, 11.46%.
5. Empirical formula
$C_{61}H_{104}N_{10}O_{13}$
6. Molecular weight
1184.
7. Ultraviolet absorption spectrum
In methanol: only terminal absorption.
8. Infrared absorption spectrum (KBr)
$\nu_{max}$: 1760, 1670–1640 cm$^{-1}$
9. Solubility
Soluble in methanol, acetone, ethyl acetate, chloroform and benzene.
Insoluble in water and hexane.
10. Thin layer chromatography
Effected on silica gel plate No. 5715 (a product of Merck & Co., Inc.) of thickness 0.25 mm. Developed with ethyl acetate, Rf value=0.10. Developed with a 10:1 by volume mixture of ethyl acetate and methanol, Rf value=0.27.

Compound (III) can be characterized by the following physical and chemical properties:
1. Colour and state
White amorphous powder.
2. Melting point
140°–150° C.
3. Specific rotation
$[\alpha]_D^{25} -57.7°$ (c=0.78, chloroform).
4. Elemental analysis
C, 61.54%; H, 8.93%; N, 12.51%.
5. Empirical formula
$C_{51}H_{87}N_9O_{10}$
6. Molecular weight 985
7. Ultraviolet absorption spectrum
In methanol: only terminal absorption.
8. Infrared absorption spectrum (KBr)
$\nu_{max}$: 1760, 1670–1640 cm$^{-1}$.
9. Solubility
Soluble in methanol, acetone, ethyl acetate and chloroform.
Insoluble in water, benzene and hexane.
10. Thin layer chromatography
The absorbent was a silica gel plate No. 5715 (a product of Merck & Co., Inc.) of thickness 0.25 mm. Developed with a 90:10:1 by volume mixture of chloroform, methanol and ammonium hydroxide, Rf value=0.2.

Compounds (II) and (III) show potent antibacterial activity against a number of infectious microorganisms, but especially microorganisms of the genus Mycobacterium and most particularly *Mycobacterium tuberculosis*, variety H 37 Rv. Accordingly, these compounds are expected to be of value in the treatment of tuberculosis.

The minimal inhibitory concentrations (MIC) of compounds (II) and (III) against various microorganisms of the genus Mycobacterium are shown in the following Table and were determined by incubating the microorganism for 7 days (in the case of *Mycobacterium smegmatis*) or 42 days (in the case of the other microorganisms) at 37° C. on Dubos liquid medium. The results are shown in the following Table.

TABLE

| Test organism | Compound (II) µg/ml | Compound (III) µg/ml |
|---|---|---|
| *Mycobacterium smegmatis* ATCC 607 | 0.05 | 3.13–6.25 |
| *Mycobacterium tuberculosis* H 37 Rv | 0.625 | 6.25–12.5 |
| *Mycobacterium intracellulare* IFM 2073 | 2.5 | 12.5–25 |

Compound (II) can be prepared by reducing Mycoplanecin. The reducing agent employed may be any agent capable of reducing the carbonyl group in the N-(α-ketobutyryl)-N-methylvalyl side chain to a hydroxy group, provided that the reducing agent and/or the conditions under which the reduction is effected are such that other parts of the Mycoplanecin molecule are not affected. Suitable reducing agents include, for example, sodium borohydride, lithium aluminum hydride or NaBH$_3$CN. Alternatively, Mycoplanecin can be treated with hydrogen gas in the presence of a catalyst (such as platinum oxide) in an organic or aqueous-organic solvent. Compound (II) may also be derived from Mycoplanecin by treating it with reducing enzymes produced by microorganisms or animals.

Compound (III) can be obtained by the hydrolysis of compound (II) or of Mycoplanecin. The hydrolysis may be effected using organic or inorganic acids in an organic solvent or in an aqueous-organic solvent. Particularly good results are achieved by the hydrolysis of such compounds using hydrochloric acid (preferably of concentration 3–5 N) at room temperature, preferably for a period of from 3 to 5 hours. However, any conventional hydrolysis method capable of removing an acyl group from a nitrogen atom may be employed.

The desired compound of formula (II) or (III) produced as described above may be isolated from the reaction mixture by conventional methods, particularly chromatography or recrystallisation. The chromatography may be effected using various carriers either separately or in combination and may, if necessary, be carried out repeatedly.

The invention is further illustrated by the following non-limiting Examples, of which Example 1 illustrates the preparation of Mycoplanecin.

EXAMPLE 1

Preparation of Mycoplanecin

To a 500 ml Sakaguchi flask were added 100 ml of a seed culture medium having a pH of 7.0 before sterilization and the following composition (percentages are w/v):

| Glucose | 1% |
|---|---|
| Glycerine | 1% |
| Oatmeal | 0.5% |
| Sucrose | 1% |
| Soybean meal | 2% |
| Casamino acid | 0.5% |
| Pressed yeast | 1% |
| Calcium carbonate | 0.1% |

Into this medium was inoculated a culture of Actinoplanes Strain 41042 (deposited under the Accession No. FERM-4504 with The Technical Research Institute of the Microbial Industry, Agency of Industrial Science and Technology, Ministry of International Trade and Industry, Japan; this strain is described in more detail in our aforementioned U.S. application Ser. No. 41,501). Reciprocal shaking culture was then carried out at 28° C. for 96 hours. The resulting culture broth was divided into 5 ml portions and each portion was inoculated into a Sakaguchi flask, each flask containing 100 ml of a production medium having a pH of 7.0 before sterilization and having the following composition (percentages are w/v):

| Glycerine | 0.5% |
|---|---|
| Sucrose | 2% |
| Soybean meal | 1% |
| Pressed yeast | 1% |
| Corn steep liquor | 0.5% |
| $CoCl_2.6H_2O$ | 0.001% |

Reciprocal shaking culture was then carried out at 28° C. for 96 hours. The resulting culture broths were combined.

To 4 liters of the combined culture broths (pH 7.2) were added 5% w/v of Celite 545 (a Trade Mark for a filter aid available from Johns Manville Product Corporation, U.S.A.) and the broth was filtered to separate the liquor from the mycelia-containing filter cake. The filtrate was extracted with 2 liters of ethyl acetate to recover its Mycoplanecin content, whilst the mycelial cake was extracted with 2 liters of acetone containing 20% v/v water; the acetone from this latter extract was then distilled off under reduced pressure and the residue was extracted with 2 liters of ethyl acetate. The ethyl acetate extracts from the filtrate and from the mycelial cake were combined, to give 4 liters of combined extracts.

These combined extracts were washed twice, each time with 1 liter of a saturated aqueous solution of sodium chloride. The washed extracts were dehydrated over anhydrous sodium sulphate and then concentrated by evaporation under reduced pressure to give 1.07 g of an oily substance.

This oily substance was dissolved in a small volume of chloroform and adsorbed on a column containing 20 g of silica gel which had previously been prepared with chloroform. The column was then washed with chloroform and impurities were eluted away using a 1:1 by volume mixture of chloroform and ethyl acetate, followed by ethyl acetate alone. The desired Mycoplanecin was then eluted with a mixed solvent containing 95% by volume ethyl acetate and 5% by volume methanol. One liter of an active fraction was separated from the eluted fractions and concentrated by evaporation under reduced pressure to give 130 mg of a white power.

110 mg of this white powder were dissolved in a small volume of chloroform and the resulting solution was passed into a 220 ml column containing Sephadex LH-20 (available from Pharmacia Co. Limited, Sweden) packed with chloroform, and which was then eluted with chloroform. Active fractions thus collected were concentrated by evaporation under reduced pressure to give 90 mg of Mycoplanecin as a white powder. This purified product showed a single spot with iodine, sulphuric acid and potassium permanganate on a silica gel thin layer chromatograph.

EXAMPLE 2

Preparation of compound (II)

To a solution of 20 g of Mycoplanecin in 200 ml of methanol were added, with ice-cooling, 1.5 g of sodium borohydride, after which the mixture was stirred for 1 hour. At the end of this time, the reaction mixture was concentrated and 500 ml of ethyl acetate were added to the residue. The mixture was then washed twice, each time with 500 ml of a saturated aqueous solution of sodium chloride. The washed mixture was dehydrated over anhydrous sodium sulphate and then concentrated by evaporation under reduced pressure to give 22 g of an oily substance. This oily substance was dissolved in 30 ml of acetonitrile and left to stand at room temperature. There were precipitated 7.2 g (yield 36%) of the desired compound (II) in the form of colourless needles.

EXAMPLE 3

Preparation of compound (III)

5 g of compound (II) were dissolved in 15 ml of a 4.5 N methanolic solution of hydrogen chloride, and the resulting solution was stirred for 4 hours at room temperature (25° C.). At the end of this time, the reaction mixture was concentrated to remove hydrogen chloride. The resulting residue was dissolved in 10 ml of chloroform and then adsorbed on a column containing 90 g of silica gel which had previously been prepared with chloroform. The column was then washed with 200 ml of chloroform and fractionally eluted with a mixed solution containing 95% by volume chloroform and 5% by volume methanol. The eluate was collected in 15 ml portions. The desired compound (III) was contained in the 17th to 24th fractions. These fractions were combined and concentrated by evaporation to give 3.85 g (yield 92.6%) of the desired compound (III).

EXAMPLE 4

Preparation of compound (III)

200 mg of Mycoplanecin were dissolved in 3 ml of a 4.5 N methanolic solution of hydrogen chloride, and the resulting solution was stirred at room temperature (25° C.) for 4 hours. After completion of the reaction, the reaction mixture was concentrated by evaporation under reduced pressure to remove hydrogen chloride. The residue was then purified as described in Example 3, to give 12 mg of the desired compound (III).

We claim:

1. Compounds of the formula (I):

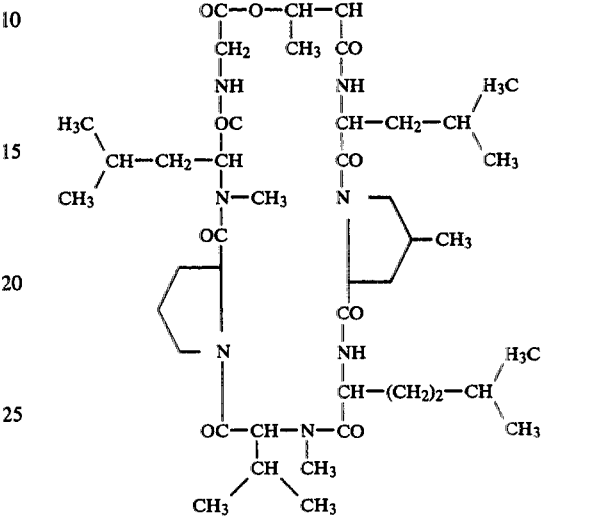

wherein R represents a hydrogen atom or an N-(α-hydroxybutyryl)-N-methylvalyl group.

2. The compound of claim 1, wherein R is hydrogen.

3. The compound of claim 1, wherein R is N-(α-hydroxybutyryl)-N-methylvalyl.

* * * * *